United States Patent
Maeno

(10) Patent No.: US 8,603,002 B2
(45) Date of Patent: Dec. 10, 2013

(54) APPARATUS AND METHOD FOR CALCULATING MICROVIBRATION FEATURE QUANTITY

(75) Inventor: Kurato Maeno, Saitama (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 15 days.

(21) Appl. No.: 13/339,390

(22) Filed: Dec. 29, 2011

(65) Prior Publication Data

US 2012/0253212 A1    Oct. 4, 2012

(30) Foreign Application Priority Data

Mar. 31, 2011   (JP) ................................. 2011-077999

(51) Int. Cl.
   *A61B 5/02*   (2006.01)
(52) U.S. Cl.
   USPC ........................................................ 600/508
(58) Field of Classification Search
   USPC ........................................................ 600/508
   See application file for complete search history.

(56) References Cited

U.S. PATENT DOCUMENTS 4,509,526 A * 4/1985 Barnes et al. ................. 600/456
2010/0069766 A1  3/2010 Kawano et al.

FOREIGN PATENT DOCUMENTS

| JP | 2006-55504 A | 3/2006 |
| JP | 2006218033 A | 8/2006 |
| JP | 2010068999 A | 4/2010 |
| JP | 2010-142456 A | 7/2010 |

OTHER PUBLICATIONS

Japanese Office Action dated Apr. 2, 2013 with English translation.

* cited by examiner

*Primary Examiner* — Joseph Dietrich
(74) *Attorney, Agent, or Firm* — Rabin & Berdo, P.C.

(57) ABSTRACT

A microvibration feature quantity apparatus includes a beat signal receiver receiving a beat signal output from a Doppler sensor, which radiates a radiation wave at a predetermined frequency to a body to be observed and senses part of the radiation wave reflected by the body to output the beat signal at a frequency corresponding to a difference in frequency between the radiation wave and the reflected part of the wave, a frequency converter transforming the received beat signal into a frequency-domain signal, and a beat signal feature quantity calculator using the frequency-domain signal to derive a beat signal feature quantity exhibiting an abrupt change with respect to time of a vibration velocity of the microvibration, thereby accurately calculating a feature quantity of the microvibration raised in the body.

7 Claims, 9 Drawing Sheets

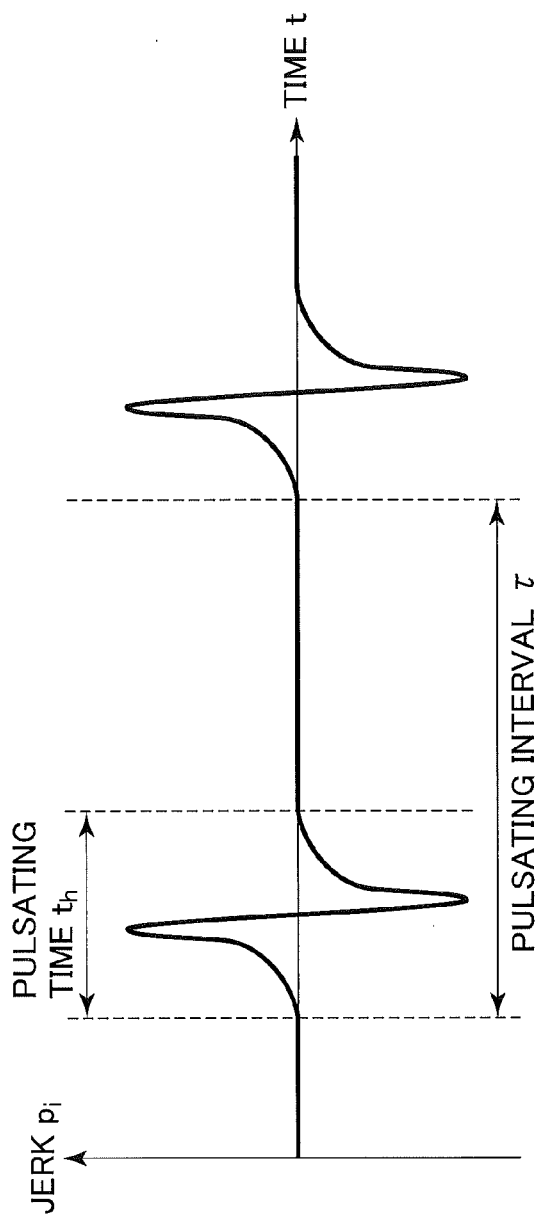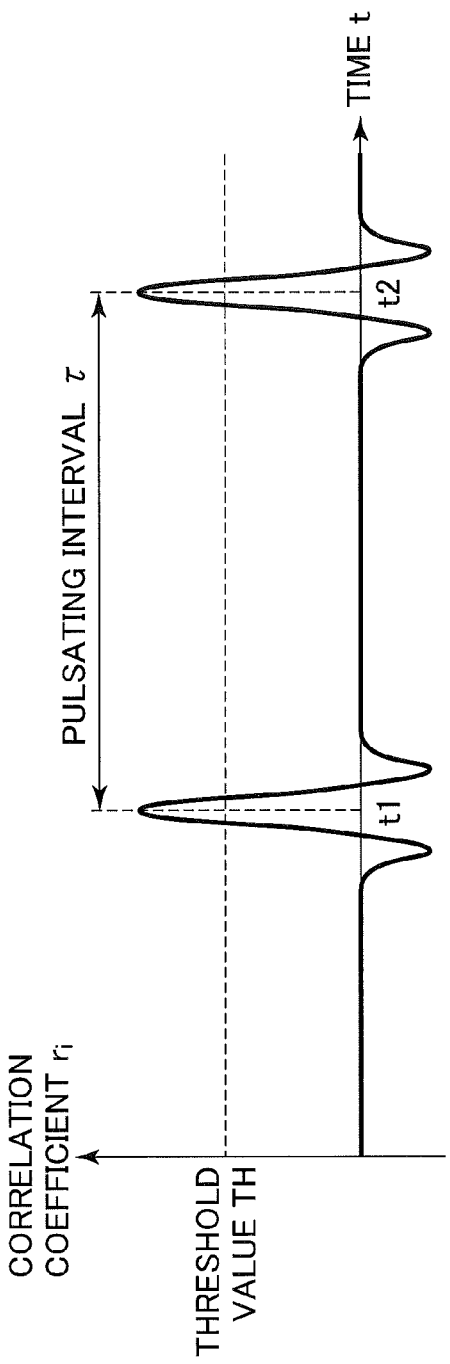
FIG. 4A
FIG. 4B

APPARATUS AND METHOD FOR CALCULATING MICROVIBRATION FEATURE QUANTITY

BACKGROUND OF THE INVENTION

1. Field of the Invention

The present invention relates to an apparatus and a method for calculating a feature quantity in connection with microvibration.

2. Description of the Background Art

In recent years, the development of technology of a system that uses outputs from a Doppler sensor to detect a heart rate has been promoted. A Doppler sensor radiates a radiation wave at a predetermined frequency to an object to be sensed and senses part of the radiation wave reflected by the object to output an output signal representative of a difference between the frequency of the radiation wave and a frequency of the reflected part. Accordingly, the use of such a Doppler sensor makes it possible to detect the heart rate of a test subject without touching the test subject. Heart rate detecting solutions using a Doppler sensor are disclosed by, for example, Japanese Patent Laid-Open Publication Nos. 2006-55504 and 2010-142456.

In the solution disclosed in Japanese '504 Publication, two sensors are used, one of which is a radio wave type of Doppler sensor that radiates a radio wave without contacting the surface of a human body to receive a reflected wave from the human body surface, and the other of which is a low-frequency sensor which is disposed near the human body surface to output an amplitude component associated with a variation in blood flow inside the human body so as to discriminate changes in heartbeat of a test person from his or her movement to measure the heart rate.

Japanese '456 Publication discloses a solution in which a Doppler sensor is embedded into a driver's seat of a vehicle, and the heart rate of a driver is estimated from outputs from the Doppler sensor. Further, in the solution, an RRI (R-R Interval), which is an interval between adjacent two peak positions (R) on heartbeat waves, is calculated with positions of the heartbeat of a driver identified so as to determine when the driver loses his or her powers of concentration or the like. In this solution, positions at which heartbeat possibly exists in time-serial data output from the Doppler sensor are predicted by means of past positional data, and information on amplitudes included in the prediction result is mainly used to identify positions of heartbeat. Further, outputs from the Doppler sensor are filtered by a band-pass filter to extract only components closely associated with the heartbeat for further processing.

However, in the above-described method disclosed in Japanese '504 Publication, the one sensor has to be disposed near a human body, thus bringing about a problematic restriction on the environment in which heartbeat is measured. In the above-described method disclosed in Japanese '456 Publication, positions of heartbeat are identified on the basis of output signals per se from the Doppler sensor or amplitudes of frequency components which are possibly associated with heartbeat, thus bringing about a difficulty in detecting heartbeat unless the sensor is very closely located to a human body.

SUMMARY OF THE INVENTION

It is therefore an object of the present invention to provide such an apparatus for calculating microvibration feature quantity that is capable of more accurately calculating a feature quantity in microvibration raised in an object to be measured, independently of an environment of measuring microvibration. It is also an object of the invention to provide a method for calculating a microvibration feature quantity with such a capability.

In accordance with the present invention, an apparatus for calculating microvibration feature quantity comprises: a beat signal receiver that receives a beat signal output from a Doppler sensor, the Doppler sensor radiating a radiation wave at a predetermined frequency to a body and sensing part of the radiation wave reflected by the body to output the beat signal at a frequency associated with a difference in frequency between the radiation wave and the reflected part; a frequency converter that transforms the received beat signal to a corresponding frequency-domain signal; and a beat signal feature quantity calculator which uses the frequency-domain signal to derive a beat signal feature quantity exhibiting an abrupt change with respect to time of a vibration velocity of the microvibration.

The apparatus for calculating microvibration feature quantity may comprise a microvibration feature quantity calculator which uses the derived beat signal feature quantity to obtain a microvibration feature quantity including at least one of a temporal position of the microvibration, an interval of the microvibration and a frequency of vibration of the microvibration.

In the apparatus for calculating microvibration feature quantity, the beat signal feature quantity calculator may obtain a beat signal in a predetermined frequency range from the frequency-domain signal to derive the beat signal feature quantity.

In the apparatus for calculating microvibration feature quantity, the frequency-domain signal may include a frequency component in the beat signal, the frequency component being dealt with a frequency change caused by a Doppler effect to be converted to a velocity, with which a weighted averaging is conducted on a power of the frequency component to thereby derive the vibration velocity in a predetermined frequency range.

In the apparatus for calculating microvibration feature quantity, the frequency-domain signal may include a frequency component in the beat signal, the frequency component being averaged with a weight corresponding to a power of the frequency component to thereby calculate the vibration velocity in a predetermined frequency range.

In the apparatus for calculating microvibration feature quantity, the beat signal feature quantity calculator may derive the beat signal feature quantity by calculating a second-order derivative with respect to time of the vibration velocity and emphasizing the microvibration from a temporal change of the vibration velocity.

In accordance with the present invention, a method for calculating a microvibration feature quantity comprises: obtaining a beat signal output from a Doppler sensor, the Doppler sensor radiating a radiation wave at a predetermined frequency to a body and sensing part of the radiation wave reflected by the body to output the beat signal at a frequency associated with a difference in frequency between the radiation wave and the reflected part; transforming the received beat signal to a corresponding frequency-domain signal; and using the frequency-domain signal to derive a beat signal feature quantity exhibiting an abrupt change with respect to time of a vibration velocity of the microvibration.

Further in accordance with the present invention, there is provided a recording medium having a computer program stored for controlling a computer, when run on the computer, to function as the apparatus for calculating microvibration feature quantity described above.

In accordance with the present invention described above, an abrupt change with respect to time of the vibration velocity of a microvibration is calculated and utilized, thereby making it possible to accurately calculate a feature quantity relating to the microvibration raised in an object to be measured, regardless of the environment of measuring microvibration.

BRIEF DESCRIPTION OF THE DRAWINGS

The objects and features of the present invention will become more apparent from consideration of the following detailed description taken in conjunction with the accompanying drawings in which:

FIGS. 4A and 4B show waveforms for use in describing how to calculate a microvibration feature quantity according to the embodiment shown in FIG. 1;

DESCRIPTION OF THE PREFERRED EMBODIMENTS

Figure 1:
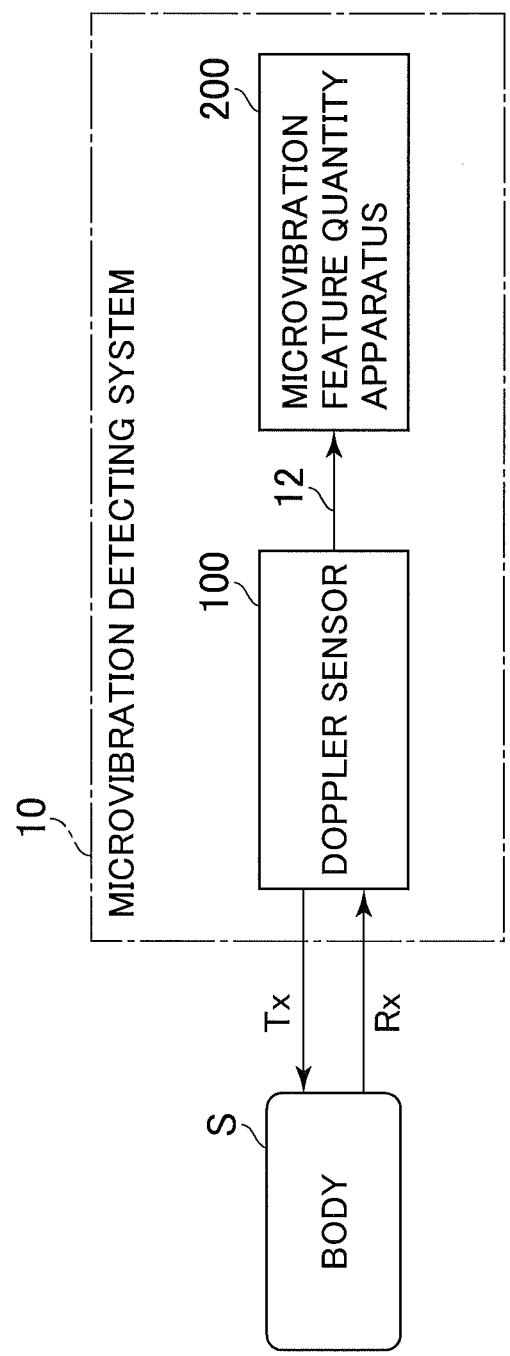
FIG. 1 is a schematic block diagram showing a system configuration including a microvibration detecting system according to a preferred embodiment of the present invention.

Preferred embodiments of the present invention will be described in detail with reference to the accompanying drawings. Like components will be denoted by the same reference numerals, and repetitive descriptions thereon will be avoided.

An illustrative embodiment of the present invention is exemplarily directed to a system adapted to detect a microvibration raised in a body to be measured, such as human body, and, more in detail, to calculate a feature quantity of a microvibration raised in such a body to be measured. In the illustrative embodiment, the "microvibration" to be dealt with is specifically directed to a vibration which may transiently be raised in a body to be measured while moving and which more finely changes than the movement inherent to the body itself. In the context, the term "movement" of a body covers not only a movement in position of the body per se but also a movement caused on the body by something in the body changing in position there inside while the body keeps its position or posture.

For example, in the illustrative embodiment, when a body to be measured is a human body, a microvibration of interest may be a vibration caused by the human body while moving in position as well as movements which may be raised by blood flow inside the human body, vibrations of his or her heart, lungs, various muscles and the like, and more specifically vibrations raised by his or her heartbeat and pulse beats, breathing, hiccups and twitching.

Further in the illustrative embodiment, bodies of interest to be measured may include an article stored in a building, such as a house or a warehouse, or even a wall or floor of a building itself. In the case of a floor of a building, for example, a temporary or transient vibration caused when a person walks or drops something, such as an article stored in a warehouse, on the floor may be considered as microvibration.

The present invention would not be restricted to the above-described specific examples of body and/or microvibration to be dealt with in the illustrative embodiment, but may be applied to other types of bodies and microvibrations. For the illustration purpose only, the illustrative embodiment will be described in connection with a human body and its heartbeat raised in the human body.

With reference first to FIG. 1, the configuration of a microvibration detecting system according to the illustrative embodiment of the invention will be briefly described. FIG. 1 schematically shows the system configuration of a microvibration detecting system 10 according to the embodiment.

The microvibration detecting system 10 generally includes a Doppler sensor 100 and a microvibration feature quantity apparatus 200 interconnected as illustrated in FIG. 1. The Doppler sensor 100 is a sensor device that is adapted to radiate a radiation wave Tx at a predetermined frequency to a body S, i.e. a human body in the present embodiment, to detect part of the radiation wave Tx reflected by the body S in the form of reflected wave Rx.

When a movement is raised in the body S, it may cause the frequency of the reflected wave Rx to be shifted from the frequency of the radiation wave Tx due to the Doppler effect. As a result, such a difference in frequency causes the radiation wave Tx and the reflected wave Rx to interfere with each other. The Doppler sensor 100 is thus adapted to detect an interference wave thus caused between the radiation wave Tx and the reflected wave Rx to resultantly output a beat signal at a frequency corresponding to the difference in frequency between the radiation wave Tx and the reflected wave Rx. As is clear from the above description, the beat signal has its frequency equal in value to the amount of Doppler shift caused by the Doppler effect on the part of the radiation wave Tx being reflected by the moving body S. Such a beat signal is a time-domain signal involving a temporal change in intensity of the interference wave.

The Doppler sensor 100 may be of any types so far as it may radiate the radiation wave Tx which can cause a Doppler effect on the radiation wave Tx when reflected by the moving body S. Applicable are Doppler sensors which may generate a radiation wave in an appropriate frequency band, e.g. an optical wave, an acoustic wave, an ultrasonic wave, a microwave. When a microwave is utilized as the radiation wave Tx, it may be preferable to use a microwave in an available frequency band, such as 10.5 GHz, 24 GHz or so, for example.

The Doppler sensor 100 operable on the basis of the principle described above is capable of remotely measuring the body S without contact with the body S. In the microvibration detecting system 10 according to the illustrative embodiment, the Doppler sensor 100 outputs a beat signal 12 to the microvibration feature quantity apparatus 200.

The microvibration feature quantity apparatus 200 is adapted to use the beat signal 12 output from the Doppler sensor 100 to calculate a microvibration feature quantity featuring a microvibration raised in a body to be measured, or a body of interest. Such microvibration feature quantities may include, for example, a temporal position at which a microvibration is raised, a time interval of microvibrations, the frequency of a microvibration, and the like.

Figure 2:
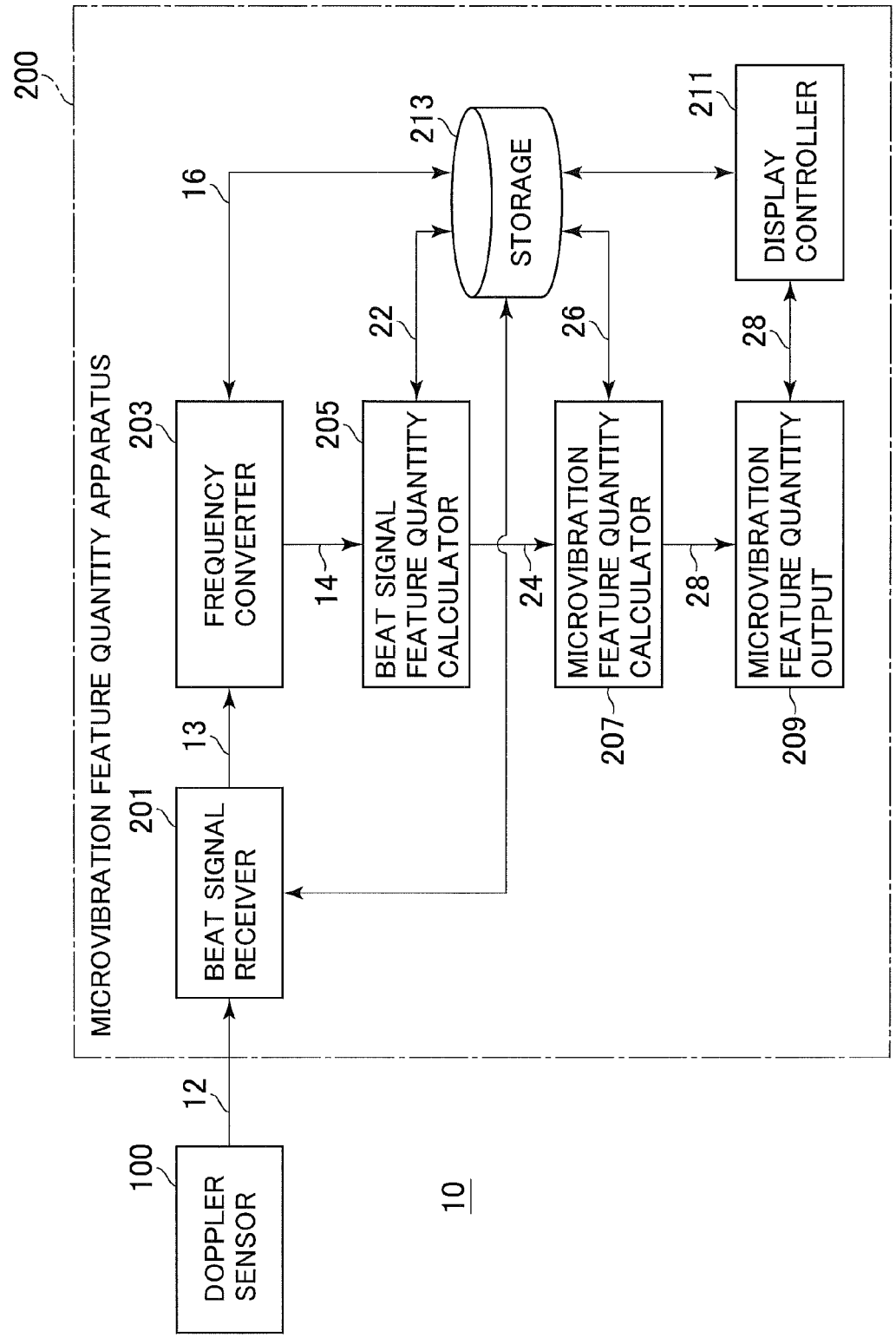
FIG. 2 is a schematic block diagram showing the configuration of an embodiment of a microvibration feature quantity apparatus included in the embodiment shown in FIG. 1.

Next, with reference to FIG. 2, the configuration of the microvibration feature quantity apparatus 200 according to the present embodiment will be described in detail. FIG. 2 schematically shows in a block diagram the configuration of the microvibration feature quantity apparatus 200. Generally, the microvibration feature quantity apparatus 200 includes a beat signal receiver 201, a frequency converter 203, a beat signal feature quantity calculator 205, and a microvibration feature quantity calculator 207 which are interconnected as illustrated in the figure. In the instant illustrative embodiment, the microvibration feature quantity apparatus 200 may additionally include a microvibration feature quantity output subsection 209, a display controller 211, and a storage 213 also interconnected as illustrated. 2. Throughout the application, like components are designated with the same reference numerals, and repetitive description thereof may be avoided for simplicity.

The beat signal receiver 201 may be implemented by a processor system including, for example, a CPU (Central Processing Unit), a ROM (Read-Only Memory), a RAM (Random Access Memory), a communication device and the like. The beat signal receiver 201 is adapted to receive or obtain a beat signal 12 output from the Doppler sensor 100 to output the beat signal 12 on a line 13 to the frequency converter 203, which will be described later. Further, the beat signal receiver 201 may also be adapted to store the received beat signal 12 in association with time information on the time and date when the beat signal 12 was received in the storage 213 in the form of history information, which will be described later. Signals or data are designated by reference numerals of interconnections conveying them.

The illustrative embodiment of the microvibration feature quantity apparatus 200 is depicted and described as configured by separate functional blocks, such as the beat signal receiver 201. It is however to be noted that such a depiction and a description do not restrict the microvibration feature quantity apparatus 200 to an implementation only in the form of hardware but may partially or entirely be implemented by software, namely, by a computer, or processor system, which has a computer program installed and functions, when executing the computer program, as part of, or the entirety of, the microvibration feature quantity apparatus 200. That may also be the case with the remaining constituent elements, such as frequency converter 203 and alternative embodiments, which will be described below. In this connection, the word "circuit", "unit" or "device" may be understood not only as hardware, such as an electronics circuit, but also as a function that may be implemented by software installed and executed on a computer.

The frequency converter 203 may be implemented also by a processor system separate from, or the same as, the beat signal receiver 201. The frequency converter 203 is adapted for converting or transforming the beat signal 13, which is a time-domain signal, output from the beat signal receiver 201 into a corresponding frequency-domain signal. In order to transform a signal expressed in the time domain into a frequency-domain signal, various methods may be applied, such as the Fourier transform, the wavelet transform, the Hadamard transform, and a matching pursuit method. The frequency converter 203 according to the present embodiment may utilize appropriate one or ones of those methods to transform a beat signal in a time-domain into a frequency-domain signal.

However, the following description will be made merely for illustration on an example where the frequency converter 203 uses the Fourier transform, more specifically, discrete Fourier transform (DFT) to transform the beat signal 13 into a corresponding frequency-domain signal.

In the illustrative embodiment, the frequency converter 203 may specifically be adapted to sample the beat signal 12, which is an analog signal received by the beat signal receiver 201, at a sampling rate of 200 Hz. The present invention is not restricted to such a specific value of sampling frequency 200 Hz, The sampling rate may be appropriately set in accordance with the type or nature of a microvibration of interest.

For a description purpose, it is assumed that the frequency converter 203 executes frequency conversion at a clock time t to execute the discrete Fourier transform on beat signal data in a temporal section or segment of T seconds. When the frequency converter 203 executes the discrete Fourier transform on a section of one second of beat signal data sampled at the rate of 200 Hz, that means the parameter T=1 and a sampling interval $\Delta t$ is equal to 0.005 seconds. In this exemplified case, the number of samples included in the data corresponding to that temporal section N is equal to 200. Then, the frequency converter 203 according to the illustrative embodiment will execute the discrete Fourier transform on a sequence of complex numbers $X_t=(x_{0,t}, x_{1,t}, \ldots, x_{j,t}, \ldots, x_{N-1,t})$ corresponding to those 200 samples of stream data, where the parameter j is a natural number from 0 to N−1, inclusive. It is to be noted that each element $X_{j,t}$ of the sequence of complex numbers $X_t$ has its real part including a sampled value of the stream data and its imaginary part equal to null.

The frequency converter 203 executes the discrete Fourier transform on the sequence of complex numbers $X_t$ to thereby produce a sequence of complex numbers $F_t=(f_{0,t}, f_{1,t}, \ldots, f_{j,t}, \ldots, f_{N-1,t})$. Here, each $f_{j,t}$ of the N elements included in the sequence of complex numbers $F_t$ generated by the discrete Fourier transform is a frequency component corresponding to an eigenfrequency, and may take a value expressed by the following expression (1):

$$f_{j,t} = \sum_{k=0}^{N-1} x_{k,t} \cdot \exp\left(-\frac{2\pi i}{N} jk\right) \tag{1}$$

where i represents an imaginary unit.

Among those components expressed by the above-described expression (1), $f_{0,t}$ corresponds to a direct-current component, and $f_{j,t}$, where j is not zero, corresponds to a frequency component at a frequency of j (Hz).

The frequency converter 203 according to the illustrative embodiment outputs the sequence of complex numbers $F_t$ 14 thus produced to the beat signal feature quantity calculator 205, which will be described later.

It is to be noted that, according to the sampling theorem, frequency components over the Nyquist frequency which is defined by half the sampling frequency, $f_s \times \frac{1}{2}$, and equal to 100 Hz in the above-described example, and thence the frequency converter 203 may not necessarily output components over the Nyquist frequency.

Further, in addition to the above-described sequence of complex numbers $F_t$, the frequency converter 203 may output the amplitude of the frequency components defined by $2|f_{j,t}|/N$ and/or a power spectrum defined by $|f_{j,t}|^2$ to the beat signal feature quantity calculator 205, which will be described later.

In addition, when the Doppler sensor 100 is of the type that radiates a radiation wave at a frequency in a microwave band and there exists a discharge tube, such as a fluorescent lamp, within the range of the radiation wave accessible, the sensor 100 may output a beat signal having a noise component mixed which corresponds to the power supply frequency of the lamp, for example, 50 Hz, 60 Hz, or so. In such a case, a band-pass filter or the like may be used to remove a frequency component corresponding to the power supply frequency for noise separation.

Further, the frequency converter 203 may store the calculated various values 16 in association with time information on the time and date when the values were calculated or the like in the form of history information in the storage 213, which will also be described later.

The beat signal feature quantity calculator 205 may also be implemented by a processor system separate from, or the same as, the beat signal receiver 201 or frequency converter 203. The beat signal feature quantity calculator 205 functions as using a frequency-domain signal 14 to which the beat signal is transformed and which is output from the frequency converter 203 to calculate out a beat signal feature quantity that features the beat signal 14.

Figure 3:
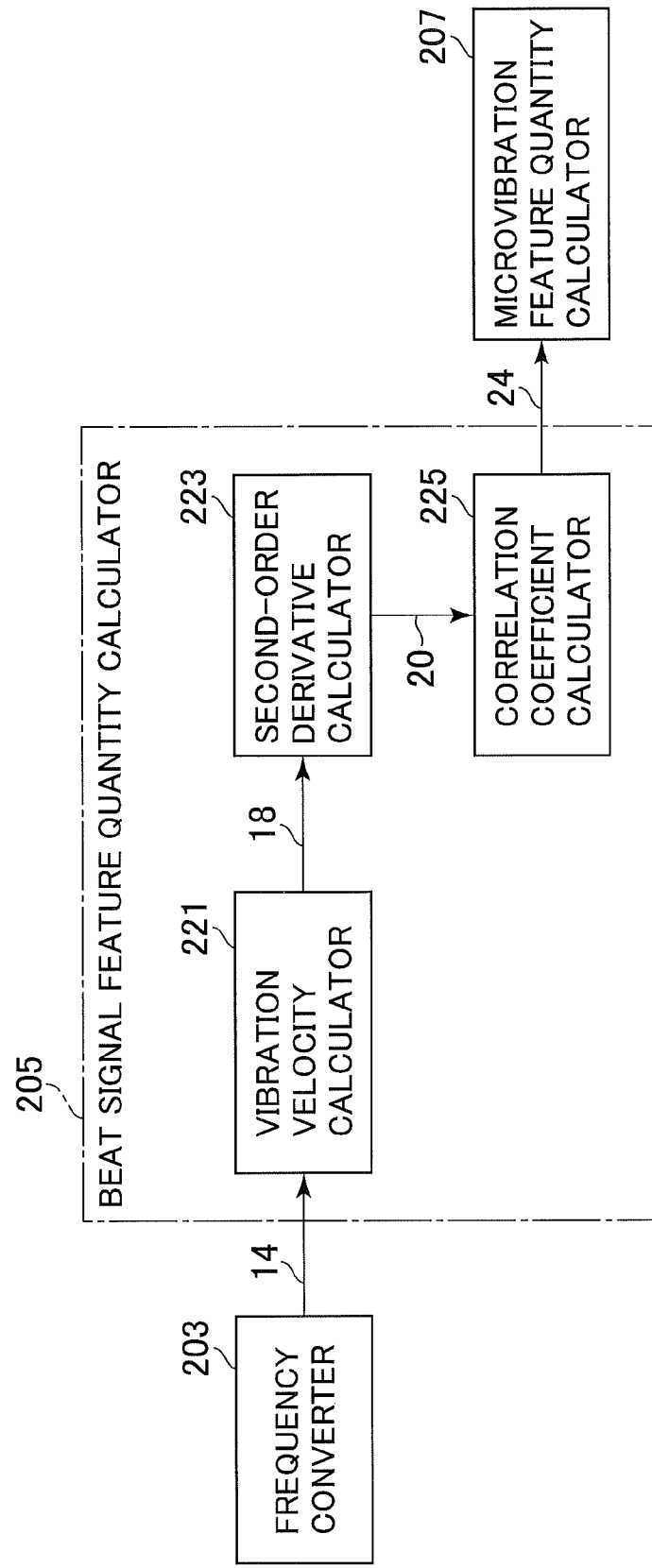
FIG. 3 is a schematic block diagram showing the configuration of the beat signal feature quantity calculator shown in FIG. 2.

Now, with reference to FIG. 3, the configuration of the beat signal feature quantity calculator 205 according to the instant embodiment will be described more in detail. FIG. 3 is a block diagram of the configuration of the beat signal feature quantity calculator 205. As can be seen from the figure, the beat signal feature quantity calculator 205 includes a vibration velocity calculator 221, a second-order derivative calculator 223, and a correlation coefficient calculator 225, which are interconnected as depicted.

The vibration velocity calculator 221 may of course be implemented by part of a processor system implementing the beat signal feature quantity calculator 205, or another processor system separate from, or the same as, the beat signal receiver 201, etc. The vibration velocity calculator 221 functions as using the frequency-domain signal 14, to which the beat signal is transformed and which is output from the frequency converter 203 in the form of sequence of complex numbers $F_t$ described above, to calculate the vibration velocity of the microvibration that is a feature quantity featuring the beat signal.

It will be described in detail how the vibration velocity calculator 221 calculates a vibration velocity. The Doppler sensor 100 radiates a radiation wave at a frequency S (Hz), part of which is reflected by a body to be measured, when microvibrating, into a frequency shifted by an amount of d (Hz), Doppler shift amount. Here, when the body moves at a velocity v (m/s), and the velocity of light is expressed as c (m/s), the relational expression of the Doppler effect is utilized to establish the relationship expressed by the following expression (2):

$$v = \frac{d \cdot c}{2S} \quad (2)$$

Further, assuming that a sequence of velocity numbers V corresponding to the sequence of complex numbers $F_t$ calculated by the discrete Fourier transform is expressed as $V=(v_0, v_1, \ldots, v_j, \ldots, v_{N-1})$ the velocity $v_j$ of each frequency component is regarded as a value expressed by the following expression (3):

$$v_j = \frac{j}{T} \cdot \frac{c}{2S} \quad (3)$$

where each frequency component of the microvibration is j/T (Hz).

The nature of the Doppler effect establishes a reversible linear relationship between frequency and velocity. Therefore, computation on frequency components may be transformed into various computation on velocity components. Relying upon this fact, it is possible to introduce computations, such as calculation of a jerk, which would usually be applied to velocity into various computations on frequency components.

In the microvibration feature quantity apparatus 200 according to the illustrative embodiment, it is assumed that the power ($|f_{j,t}|^2$) at each frequency obtained by the discrete Fourier transform is a quantity of a body when moving at a velocity corresponding to the frequency. As a result, the average velocity of movements of the body S of interest may be resultant from dividing the summation of values expressed with $v_j \cdot |f_{j,t}|^2$ with respect to the parameter j by the summation of powers $|f_{j,t}|^2$ of frequencies also with respect to the parameter j.

When a body of interest is a human body as a representative of biologic body, his or her heartbeat may be regard as microvibration of the human body more finely changing than so-called body movements caused by his or her muscular exercise. It is generally recognized that the velocity of blood flowing through aortas, which are the largest blood vessels in human being, varies up and down in response to the heartbeat within a range of approximately 0 to 1.2 (m/s), and in peripheral blood vessels branching from the aortas, the velocity goes up to the maximum of 0.4 to 1.2 (m/s) in arteries and becomes lower than this in smaller arteries.

Under those circumstances, a Doppler shift amount d corresponding to a velocity of 1.2 (m/s) will be 192 Hz when the frequency S of a radiation wave is 24 GHz, i.e. microwave range. It can therefore be understood that, in view of the entire human body, it is possible to observe a Doppler shift resultant from the movements caused by heartbeat within an extensive range from 0 to almost 200 Hz. Further, the portions of a human body which have blood flow are boarder in area as approaching his or her peripheral. It can therefore be said that the lower the blood velocity, the broader the reflection area. Therefore, a smaller Doppler shift tends to express a higher frequency power.

More specifically, each time heartbeat pulsates, the powers of the frequency components in such a broad range extending from 0 to almost 200 Hz instantaneously go up and down in synchronism with the pulsating heartbeat. Further, the frequency lowers from 200 Hz, the frequency power tends to become higher.

However, a frequency shift resultant from the Doppler effect is a quantity dependent upon the directional component of a wave of interest, such as microwave, in the direction in which the wave arrives. In addition, the direction in which a wave arrives may often be different from the direction in which a body to be measured moves, so that a Doppler shift observed by the Doppler sensor may often be lowered from above-described range. Further, for the same reason, when the Doppler sensor is directed to the front of a person, an amount of Doppler shift caused by pulsating of his or her heart or on his or her body surface may be predominant in some cases. The movements raised by pulsating inside a body may be directed in various directions and include many components not matched to the direction in which the Doppler wave arrives. Therefore, frequencies observed may be lower in average lower than the frequency corresponding to the velocity of the actual movement. That may cause Doppler shifts not evenly to be distributed over the frequency range from 0 to almost 200 Hz but the lower frequency components to be much more influenced by the pulsating.

Further, the Doppler shift observed by a Doppler sensor may involve so-called environmental noise, such as a long-period micro-oscillation of a building structure caused by wind or external vibration. Usually, such environmental noise may be observed often in a low-frequency range lower than 10 Hz. Therefore, according to the instant illustrative embodiment, the vibration velocity calculator 221 is adapted, to calculate the vibration velocity of microvibration in such a fashion that the higher-frequency range excluding the low-frequency range rich in environmental noise, defined by the parameter j falling in a range of L to H, is utilized to calculate a vibration velocity $v_{VIB,t}$ on the basis of the following expression (4). The vibration velocity $v_{VIB,t}$ is defined by taking frequency power average on the microvibration of a body to be measured at a clock time t. Specifically with the present embodiment, $v_{VIB,t}$ is a vibration velocity fluctuating in response to pulsating heartbeats of a human body:

$$v_{VIB,t} = \frac{\sum_{j=L}^{H-1} v_j \cdot |f_{j,t}|^2}{\sum_{j=L}^{H-1} |f_{j,t}|^2} \quad (4)$$

The term "frequency power average" herein is a weighted averaging weighted with frequency power. For example, under the above-described sampling conditions, the vibration velocity calculator 221 eliminates the frequency band under 10 Hz including many environmental noises. Since the lower frequency components the stronger influence on heartbeat, a frequency range up to 100 Hz, such as a range from 10 Hz to 100 Hz, inclusive, can be used in a similar way to calculate out a vibration velocity $V_{VIB,t}$ at a clock time t. It is noted in the above-described example that the sampling is carried out at the rate of 200 Hz, so that frequency components higher than 100 Hz are not included. In order to obtain frequency components higher than that, the sampling rate may be increased and the parameter H may be set to a higher value.

In short, in the vibration velocity calculator 221 according to the illustrative embodiment, when a body to be measured is remotely observed by means of a Doppler sensor, a beat signal output from the Doppler sensor is transformed into a frequency-domain signal, and a low frequency region corresponding to environmental noises apt to be superimposed on the beat signal and observed in the low frequency region is excluded from the processing, and thereafter a frequency power average is calculated. That may allow, when a body to be measured is remotely observed by using a Doppler sensor, the processing to be carried out with a variety of noise influences excluded, regardless of the environment of measuring microvibration. Further, when an environmental noise at a known frequency, such as power-supply noise at 50 Hz, 60 Hz or so, is mixed, the power of the corresponding frequency components, 50 Hz, 60 Hz or so and therearound in the above example, may be set to "0" for calculation to thereby exclude the environmental noise.

The vibration velocity $v_{VIB,t}$ thus obtained has a time-serially fluctuable component which instantaneously changes up and down in response to a pulsating movement of heartbeat.

Further, as is clear from the above-described expression (3), the Doppler effect establishes a linear relationship between the velocity of microvibration $v_j$ (m/s) and the frequency of microvibration j/T (Hz). Therefore, as a quantity alternative to the velocity of microvibration, the vibration velocity calculator 221 may deal with an average power frequency with the velocity of microvibration $v_j$ replaced by the frequency of microvibration j/T as a vibration velocity to calculate the average power frequency.

The vibration velocity calculator 221, FIG. 3, outputs the vibration velocity 18 of the microvibration thus calculated to the second-order derivative calculator 223, which will be described later. Further, it is preferable that the vibration velocity calculator 221 stores the value of the calculated vibration velocity in association with time information on the time and date when this value is calculated in the storage 213 in the form of history information.

The second-order derivative calculator 223 may of course be implemented by part of a processor system implementing the beat signal feature quality calculator 205, or another processor system separate from, or the same as, the beat signal receiver 201 or the vibration velocity calculator 221, etc. The second-order derivative calculator 223 serves as using the vibration velocity 18 of microvibration calculated by the vibration velocity calculator 221 to calculate the second-order derivative of the vibration velocity 18 of the microvibration with respect to time. The second-order derivative of a vibration velocity with respect to time plays the role of, as will be described below, an index value representing an abruptly changing fraction of the vibration velocity with respect to time. As an index value representative of an abruptly changing fraction, the second-order derivative of a vibration velocity with respect to time is calculated, and a cross-correlation coefficient of the derivative with a reference waveform may be used. Further, an acceleration, the derivative of a vibration velocity with respect to time, is calculated to derive a cross-correlation coefficient of the acceleration with more abrupt reference waveform, and the temporal change in vibration velocity is used to emphasize the microvibration to serve as such an index value.

It is possible to model the heartbeat to be dealt with in the illustrative embodiment into a phenomenon that a couple of temporal sections alternate: one section corresponding to pulsating at an extremely short interval of time, occurring at a frequency of once or twice per second, and the other section not pulsating over a long interval of time. The vibration velocity 18 of microvibration calculated by the vibration velocity calculator 221 has a pulsating component that instantaneously goes up and down in response to a pulsating movement at the extremely short interval of time, whereas it takes a smaller value in the other section not pulsating and is smaller in change. Further, it is possible to model a microvibration other than heartbeat caused in a human body, such as pulse beats, hiccups or twitching, in a similar way. Accordingly, the beat signal to be observed is a signal having the frequency components distributed over the above-described broad range which are modulated with a signal based upon the long period constituted of the pulsating section at the frequency of approximately 0.1 to 1 Hz and the non-pulsating section. In order to analyze such a periodical vibration, the microvibration feature quantity apparatus 200 according to the illustrative embodiment utilizes jerk (m/s$^3$) that is the second-order derivative of a vibration velocity $v_{VIB,t}$ with respect to time to emphasize the pulsating section. More specifically, the pulsating section is characteristic in that the vibration velocity abruptly goes up and down on the time axis. Hence, the jerk exhibits on the time axis the nature of tending to instantaneously and significantly rise up and fall down only in the pulsating section, and to take only a small value and fluctuate small in the non-pulsating section.

The second-order derivative calculator 223 stores vibration velocities output from the vibration velocity 18 calculator 221 over a period of several clock times, and calculates jerk $P_t$ at a clock time t on the basis of the following expression (5)

$$P_t = \frac{v_{VIB,t} + v_{VIB,t-2} - 2v_{VIB,t-1}}{(\Delta t)^2} \quad (5)$$

Further, when the vibration velocity calculator 221 outputs an average power frequency as a vibration velocity, the second-order derivative calculator 223 is also capable of calculating a second-order derivative of the average power frequency with respect to time in the same way as in the expression (5).

The second-order derivative thus calculated, e.g. jerk, which is the second-order derivative of a vibration velocity, taking an example of heartbeat pulsation, may often take such a waveform as plotted in FIG. 4A, which has portions, corresponding to the time of pulsating heartbeat, changing to form impulse-like waveforms each having a single positive- and a single negative-going peak on the time axis, as well as the remaining portions being smaller in value and almost unchangeable.

In the microvibration feature quantity apparatus 200 according to the illustrative embodiment, a beat signal carrying information on a microvibration is transformed into a frequency-domain signal, of which a frequency region other than one apt to be influenced by environmental noises or the like is differentiated in the second order with respect to time as described above, thus making it possible to advantageously separate a pulse waveform imputed to the microvibration. In this way, the microvibration feature quantity apparatus 200 according to the embodiment is capable of accurately calculating a feature quantity relating to microvibration although remotely observing an object to be measured by means of a Doppler sensor.

The second-order derivative calculator 223 outputs the value of the second-order derivative 20 with respect to time of the vibration velocity 18 thus calculated to the correlation coefficient calculator 225 which will be described later. Further, it is preferable that the second-order derivative calculator 223 stores the calculated value of the second-order derivative with respect to time of the vibration velocity in association with time information on the time and date when this value is calculated in the storage 213 in the form of history information 22.

Now, the correlation coefficient calculator 225 may be implemented by part of a processor system implementing the beat signal feature quality calculator 205, or another processor system separate from, or the same as, the beat signal receiver 201 or the vibration velocity calculator 221, etc. The correlation coefficient calculator 225 is adapted to use the second-order derivative 20 with respect to time of the vibration velocity calculated by the second-order derivative calculator 223 and a reference waveform relating to the microvibration of interest to calculate a cross-correlation coefficient between the second-order derivative and the reference waveform. This cross-correlation coefficient may be utilized as a value representing to how much extent the microvibration exists at a clock time t.

As shown in FIG. 4A, the second-order derivative with respect to time of the vibration velocity takes impulse waveforms whose positive and negative peaks correspond to heartbeats. According, a correlation coefficient, more specifically cross-correlation coefficient, is calculated between the reference waveform of the second-order derivative of a microvibration of interest, i.e. heartbeat in the embodiment, and the calculated second-order derivative, thus making it possible to advantageously identify a temporal position at which the microvibration, such as heartbeat, of interest is raised.

It is to be noted that a reference waveform for use in calculating a cross-correlation coefficient may be defined by using various kinds of window function appropriate for the nature, such as waveform, of a second-order derivative of interest, to which the invention may not particularly restrictive. With the present embodiment, the correlation coefficient calculator 225 is adapted to define a pulse wave $w_k$ by the following expression (6) with a Gaussian window used as a window function to use the pulse wave $w_k$ as a reference waveform of microvibration:

$$w_k = \exp\left[-\frac{(k-h/2)^2}{\delta^2}\right] \cdot \sin\left(\frac{2\pi k}{h}\right) \quad (6)$$

where the parameters h and δ are of featuring a pulse wave utilizing a Gaussian window for use in defining the length of a section and the sharpness of a change of the reference waveform. Further, in the above-described expression (6), the parameter k is an integer number of 0 to h−1, inclusive.

In general, a typical electrocardiography (ECG or EKG) tracing of the cardiac cycle observable in synchronism with heartbeat includes a time-serial string of Q, R and S waves, i.e. QRS complex, which exhibits the most characteristic impulse waves and has its temporal duration, QRS duration, typically extending approximately from 0.06 to 0.10 seconds, inclusive. This impulse waves are an electrical signal for driving heart muscle, and cause the heart muscle to be driven so as to flow blood. Accordingly, the movement of heart muscle and change in blood flow continue in a period of time longer than the QRS duration. By the way, the instant illustrative embodiment is directed to employ a Doppler sensor to sense microvibration caused by the activity of heart muscle or the flow of blood through blood vessels, and therefore the QRS duration may often be shorter than the pulse duration of jerk as shown in FIG. 4A.

However, the jerk of microvibration to be detected, such as heartbeat, is in a section in which the tendency of increase and decrease in acceleration abruptly changes. Therefore, computation needed for identifying a temporal position at which the microvibration is raised may not necessarily extend over the entire period of time but be sufficient with only such a section that abruptly changes in value being focused.

Then, as shown in FIG. 4A, when heartbeat pulsates over a period of time $t_h$ (seconds), the values of the parameters of the reference waveform included in the above-described expression (6) may be adjusted such that the reference waveform for use in calculating a cross-correlation coefficient takes a value similar to one appearing in that pulsating period of time. In detail, in the correlation coefficient calculator 225 according to the illustrative embodiment, the values of the parameter h and the parameter δ denoting the sharpness of a change are selected such as to render the reference waveform approximately equal in length to the vibration time of microvibration of interest $t_h$ (seconds), e.g. the pulsating time of heartbeat in the embodiment.

Figure 5:
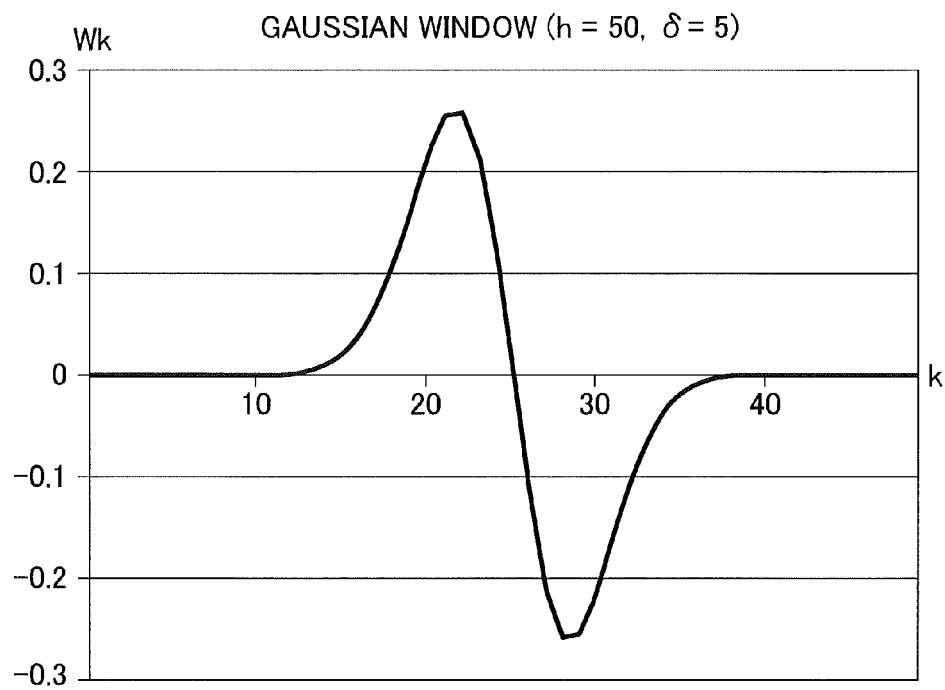
FIGS. 5 and 6 show examples of a reference waveform of microvibration.

For example, FIG. 5 shows a reference waveform for detecting jerk in heartbeat in a case where a Gaussian window is set with h=50, corresponding to 0.25 seconds under the above-described sampling conditions, and δ=5. The Gaussian window includes a section in which the value significantly changes extends in the central area and occupies approximately half of the entire section. Such a reference waveform may be utilized, thus being able to advantageously calculate a cross-correlation coefficient of jerk.

More in specific, the correlation coefficient calculator 225 uses the following expressions (7) and (8) to thereby calculate a cross-correlation coefficient between the second-order derivative with respect to time of a vibration velocity and a reference waveform, i.e. a cross-correlation coefficient at a clock time t $r_t$.

$$r_t = \frac{\sum_{i=0}^{h-1} w_i \cdot (p_{t-i} - \overline{p}_t)}{\sqrt{\sum_{i=0}^{h-1} w_i^2} \cdot \sqrt{\sum_{i=0}^{h-1} (p_{t-i} - \overline{p}_t)^2}} \quad (7)$$

$$\overline{p}_t = \frac{1}{h} \sum_{j=0}^{h-1} p_{t-j} \quad (8)$$

With this processing, for example, a cross-correlation coefficient as shown in FIG. 4B is calculated.

The above description is specifically directed to jerk that is a second-order derivative with respect to time of a vibration velocity. However, the same or similar processing may also be applied to a case where an average power frequency is dealt with as a vibration velocity.

Figure 6:
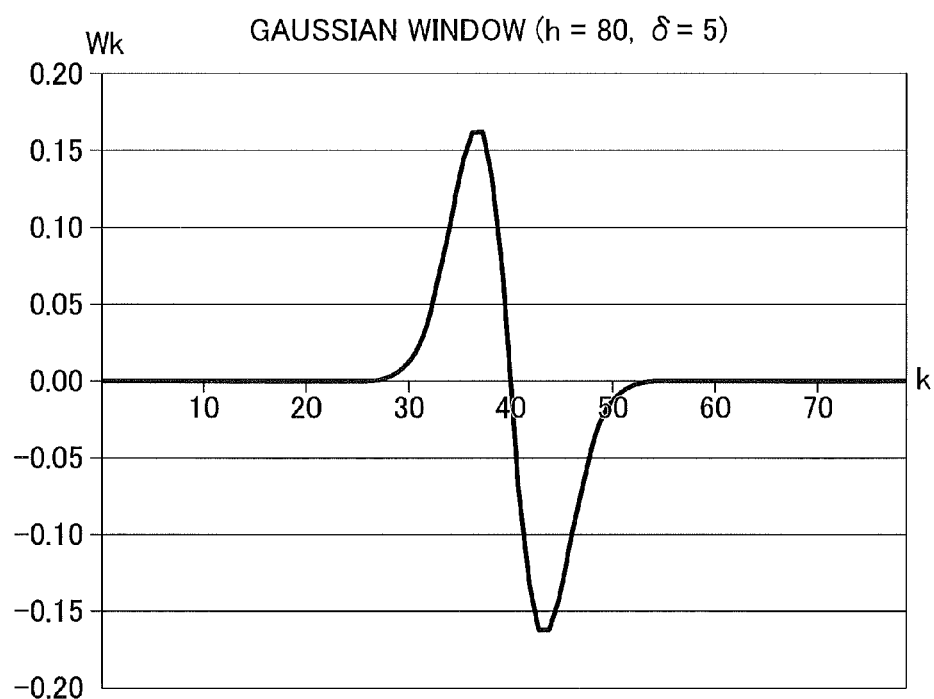

Further, the processing by means of a similar reference waveform is applicable not only to microvibration, such as heartbeat, caused by the movement of a human body but also to microvibration of a floor raised by the impact of a material body dropping. When observing microvibration of a floor caused by the impact of a body dropping, the parameters of the Gaussian window defined by the above expression (6) may be required to be modified depending on the size or weight of a dropping body to be observed. When the weight of a body of interest is relatively light, it is possible to execute similar processing by using a Gaussian window where h=80 and δ=5 as shown in FIG. 6.

When the correlation coefficient calculator 225 calculates a cross-correlation coefficient 24 by processing as described above, it outputs the calculated cross-correlation coefficient 24 to the microvibration feature quantity calculator 207. Further, the correlation coefficient calculator 225 may store those calculated values 26 in association with time information on the time and date when they are calculated in the storage 213 in the form of history information.

The configuration of the beat signal feature quantity calculator 205 according to the illustrative embodiment has been described in detail with reference to FIGS. 3 to 6. Now, returning to FIG. 2, the microvibration feature quantity calculator 207 included in the microvibration feature quantity apparatus 200 according to the embodiment will be described in detail.

The microvibration feature quantity calculator 207 may be implemented also by a processor system separate from, or the same as, the beat signal receiver 201 or the frequency converter 203, etc. The microvibration feature quantity calculator 207 is adapted for using the beat signal feature quantity including the vibration velocity of microvibration, the second-order derivative with respect to time of the vibration velocity, the cross-correlation coefficient relating to the second-order derivative and the like which are calculated by the beat signal feature quantity calculator 205 to calculate out a microvibration feature quantity that features microvibration raised in a body of interest. Such a microvibration feature quantity calculated by the microvibration feature quantity calculator 207 may be, for example, the temporal position, interval and vibration frequency of microvibration.

It will be described in more detail how the microvibration feature quantity calculator 207 calculates or derives a microvibration feature quantity. The cross-correlation coefficient $r_t$ that is one of the beat signal feature quantities calculated by the microvibration feature quantity calculator 207 is a statistical index denoting the degree of similarity between two data, e.g. the calculated second-order derivative and the reference waveform in the embodiment, as described above, and has its value taking an actual number from −1 to 1, inclusive. The cross-correlation coefficient $r_t$, when having its value approximate to "1", means that the two data are similar. The cross-correlation coefficient $r_t$, when having its value approximate to "0", means that the two data are not similar. Further, the cross-correlation coefficient $r_t$, when having its value approximate to "−1", means a situation like that the two data are opposite in sign to each other.

Therefore, the microvibration feature quantity calculator 207 is adapted to compare the calculated cross-correlation coefficient $r_t$ with a predetermined threshold value TH to identify the temporal position of a peak value higher than the predetermined threshold value TH as a temporal position at which microvibration is raised. For example, when the time serial tracing of the cross-correlation coefficient $r_t$ as shown in FIG. 4B is calculated, the microvibration feature quantity calculator 207 determines that microvibration is raised at clock times t1 and t2.

Here, the above-described threshold value TH may take its value appropriately set in accordance with a type of microvibration of interest, and may be set to a value approximately from 0.5 to 0.7, inclusive, for example.

The microvibration feature quantity calculator 207 also identifies the time interval between adjacent two peak positions, τ=t2−t1 in the example of FIG. 4B, as the interval of microvibration. Moreover, the microvibration feature quantity calculator 207 is capable of deriving the inverse number of the interval of microvibration to thereby obtain the frequency of vibration of the microvibration, which is a heartbeat rate when heartbeat is dealt with as microvibration.

The microvibration feature quantity calculator 207 may be adapted for calculating only some, or all, of the above-described microvibration feature quantities.

In addition, the microvibration feature quantity calculator 207 may be adapted not only to detect the peak position of a cross-correlation coefficient by means of comparison with a threshold value but also to search for the peak of a cross-correlation coefficient at a predetermined interval of time, approximately 0.3 seconds in the example shown in FIG. 6, in accordance with the length of a section of the reference waveform, e.g. 0.25 seconds with the reference waveform shown in FIG. 6, for use in calculating the cross-correlation coefficient to deal with the detected peak position as a timing at which the microvibration takes place.

Further, in a case where interest is particularly directed to microvibration, such as heartbeat, which does not significantly fluctuate in an extremely short interval of time, averaging with respect to time may be performed such as calculating an autocorrelation coefficient from the second-order derivative calculated over a temporal section of several seconds and identifying the peak position of the autocorrelation coefficient as a pulsating position, thereby improving the accuracy of calculation. Further, abnormal values resultant from noise or the like may be excluded prior to the processing described above, thereby being able to further improve the accuracy of calculation.

The microvibration feature quantity calculator 207 outputs the various microvibration feature quantity 28 thus calculated to the microvibration feature quantity output subsection 209, which will be described later. Further, the microvibration feature quantity calculator 207 may be adapted to store the calculated microvibration feature quantities in association with time information on the time and date when those values 26 are calculated in the storage 213 or the like in the form of history information, which will also be described later.

Description will now be made on the microvibration feature quantity output subsection 209, which may also be implemented by a processor system separate from, or the same as, the beat signal receiver 201 or the vibration velocity calculator 221, etc. The microvibration feature quantity output subsection 209 serves as outputting the microvibration feature quantity 28 derived by the microvibration feature quantity calculator 207 to outside utility circuitry in a variety of appropriate forms. The microvibration feature quantity output subsection 209 is capable of, for example, outputting a calculated microvibration feature quantity to an output device, such as a display, provided in the microvibration feature quantity apparatus 200 or in an external device with which the microvibration feature quantity apparatus 200 may communicate although they are not specifically shown. Further, the microvibration feature quantity output subsection 209 may also be adapted for transmitting a calculated microvibration feature quantity in the form of data to a variety of devices that are directly, or over various kinds of telecommunications networks, such as the Internet, connected to the microvibration feature quantity apparatus 200. Further, the microvibration feature quantity output subsection 209 may also be capable of allowing a calculated microvibration feature quantity to be outputted on a hardcopy reproduction device, such as a printer, to output it in a visualized form, such as a printed material.

Again, the display controller 211 may be implemented also by a processor system separate from, or the same as, the beat signal receiver 201 or the frequency converter 203, etc. The display controller 211 functions as controlling an output device, such as a display unit, not specifically shown, in order to display various results of calculation obtained by the microvibration feature quantity apparatus 200 in the form of visual images and/or sound. The display controller 211 may further be adapted for controlling display of such various results of calculation on an output device possibly included in various kinds of device provided outside the microvibration feature quantity apparatus 200 in order to visually or acoustically display such results.

The storage 213 is an example of storage device included in the microvibration feature quantity apparatus 200 of the instant illustrative embodiment. In the storage 213, there may be stored various results of calculation obtained by the microvibration feature quantity apparatus 200 of the embodiment, a variety of parameters needed to be stored when the apparatus 200 executes some processing, intermediate data or history of the processing, various databases and program sequences, or the like. The storage 213 is arranged so that it may appropriately be read and written by the constituent functional units, such as the beat signal feature calculator 205, included in the microvibration feature quantity apparatus 200.

The examples of function of the microvibration feature quantity apparatus 200 have been described above according to the preferred illustrative embodiment. The above-described constituent components may be implemented by general-purpose processors and/or circuits, or alternatively or additionally may be composed of hardware specifically designed for the functions of those components. Further, those functions may entirely be implemented by a processor system or systems. The configuration of the microvibration feature quantity apparatus 200 may thus appropriately be implemented by the state of art possibly available at the time when the embodiment is to be implemented.

Further, the functions of the microvibration feature quantity apparatus according to the illustrative embodiment described above may be attained in the form of computer program or programs, which may be installed in a processor system, such as personal computer, to run so as to implement those functions. Computer-readable recording medium or media may be provided in which such a computer program or programs are stored. The recording media may be, for example, a magnetic disk, an optical disk, a magneto-optical disk, a semiconductor storage, such as flash memory, or the like. Further, the above-described computer program or programs may be distributed over, for example, a telecommunications network without using recording media.

Figure 7:
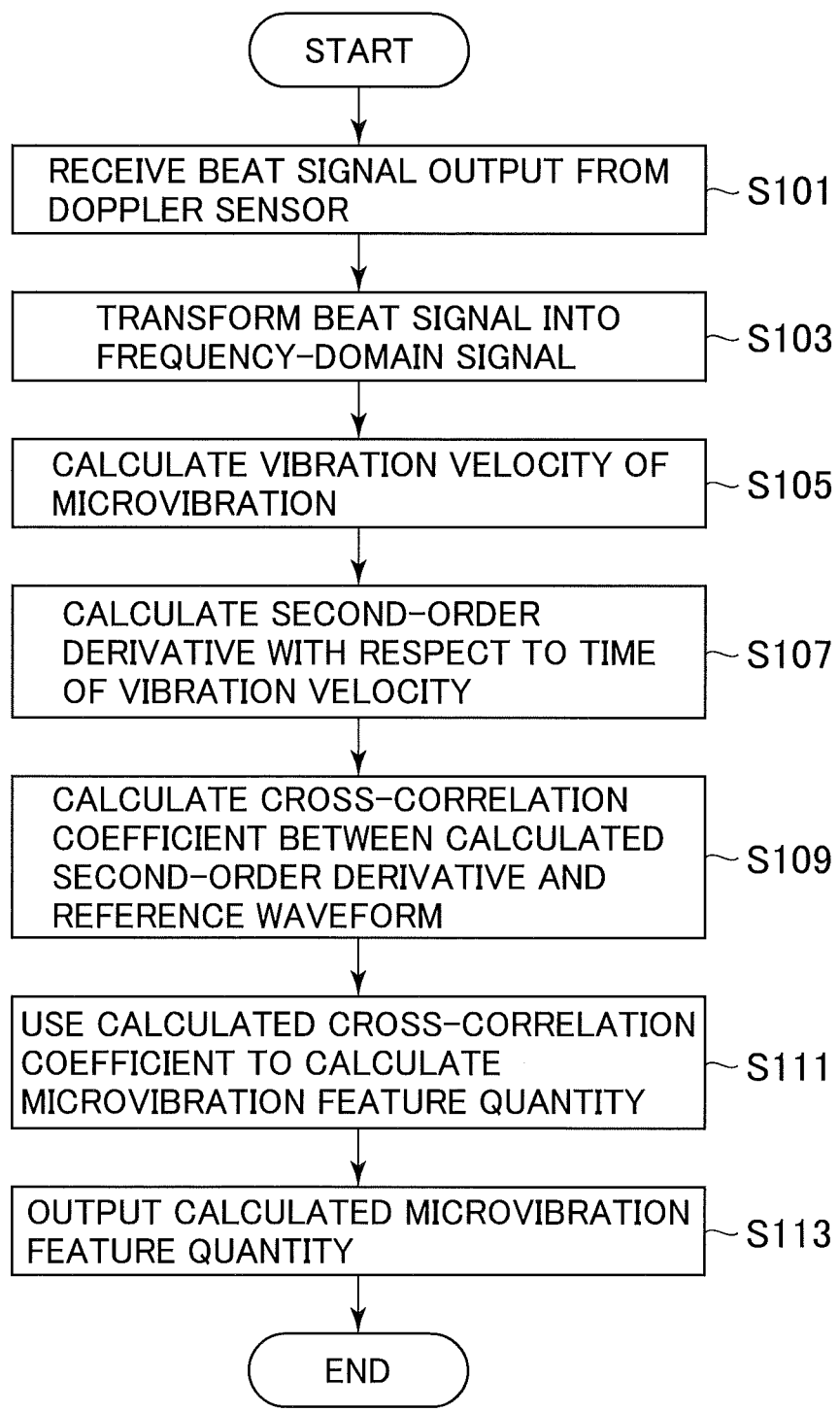
FIG. 7 is a flowchart useful for understanding how to calculate a microvibration feature quantity in the embodiment shown in FIG. 1.

Next, with reference to FIG. 7, description will be made on an example of control flow of calculating a microvibration feature quantity according to the instant illustrative embodiment. FIG. 7 is a flowchart useful for understanding such an example of control flow.

First, the beat signal receiver 201 of the microvibration feature quantity apparatus 200 receives or obtains a beat signal 12 output from the Doppler sensor 100 (step S101) to output the latter to the frequency converter 203.

Next, the frequency converter 203 of the microvibration feature quantity apparatus 200 applies any appropriate one of the various methods capable of time-frequency conversion to the beat signal output from the beat signal receiver 201 to thereby transform the beat signal 12, which is a time-domain signal, into a frequency-domain signal 14 (step S103). The frequency converter 203 in turn outputs the frequency domain signal 14, to which the beat signal is transformed, to the beat signal feature quantity calculator 205.

Subsequently, the vibration velocity calculator 221 of the beat signal feature quantity calculator 205 uses the frequency-domain signal 14 to which the beat signal is transformed to derive the vibration velocity of the microvibration (step S105), and outputs the vibration velocity 18 of the microvibration to the second-order derivative calculator 223.

The second-order derivative calculator 223 utilizes the calculated vibration velocity 18 of the microvibration to calculate the second-order derivative 20 with respect to time, i.e. jerk, of the vibration velocity (step S107). The second-order derivative calculator 223 in turn outputs the calculated second-order derivative with respect to time of the vibration velocity to the correlation coefficient calculator 225.

The correlation coefficient calculator 225 uses the calculated second-order derivative 20 with respect to time of the vibration velocity 18 and a reference waveform defined with a predetermined window coefficient to calculate a cross-correlation coefficient 24 between these two data (step S109). The correlation coefficient calculator 225 then delivers the calculated cross-correlation coefficient 24 to the microvibration feature quantity calculator 207.

The microvibration feature quantity calculator 207 uses the cross-correlation coefficient 24 output from the correlation coefficient calculator 225 to derive a microvibration feature quantity including the temporal position, interval and frequency of vibration of the microvibration, and the like (step S111). The microvibration feature quantity 28 calculator 207 then outputs the calculated microvibration feature quantity 28 to the microvibration feature quantity output subsection 209.

Thereafter, the microvibration feature quantity output subsection 209 outputs the calculated various microvibration feature quantity 28 in the form of appropriate formats (step S113). Thus, the microvibration feature quantity 28 calculated by the microvibration feature quantity apparatus 200 according to the embodiment will be provided to the user in a format appropriate for the user.

Figure 8:
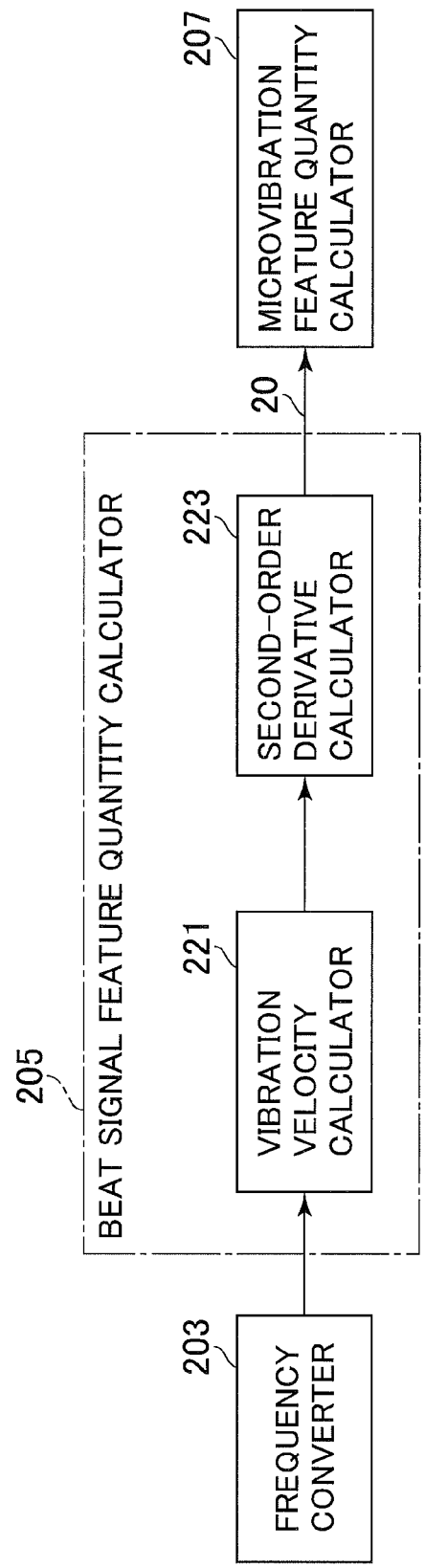
FIG. 8 is a schematic block diagram, like FIG. 3, showing an alternative embodiment of the beat signal feature quantity calculator shown in FIG. 2.

Alternative embodiments of the microvibration feature quantity apparatus 200 according to the invention will now briefly be described. The illustrative embodiment described above generally includes the beat signal microvibration feature quantity calculator 205 comprised of three processing sections, i.e. the vibration velocity calculator 221, the second-order derivative calculator 223, and the correlation coefficient calculator 225. However, as shown in FIG. 8, according to an alternative embodiment, the beat signal microvibration feature quantity calculator 205 may include only the vibration velocity calculator 221 and the second-order derivative calculator 223 but not the correlation coefficient calculator 225, so that the microvibration feature quantity calculator 207 is capable of calculating various kinds of microvibration feature quantity.

In the alternative embodiment, the second-order derivative calculator 223 may produce the calculated second-order derivative 20 with respect to time of a vibration velocity to the microvibration feature quantity calculator 207.

The microvibration feature quantity calculator 207 according to the alternative embodiment then can take the features of the time-serial data of second-order derivative as shown in FIG. 4A as well as the peak interval, fluctuation in interval between the positive and negative peaks, fluctuation in positive-going of the impulse waveforms and the like as shown in FIG. 4A to identify a temporal position at which the microvibration of interest is raised.

In the alternative embodiment described above, various data processing by means of a beat signal are executed in the microvibration feature quantity apparatus 200. However, the respective functions of the microvibration feature quantity apparatus 200 described above may be installed in the same apparatus as the Doppler sensor 100 is. Alternatively, only the Doppler sensor 100 may be disposed in a space including an object to be measured, and the respective functions of the microvibration feature quantity apparatus 200 may be implemented in a remote server or the like. Further, some of the functions of the microvibration feature quantity apparatus 200 as described above may be installed in the same apparatus as the Doppler sensor 100.

Figure 9:
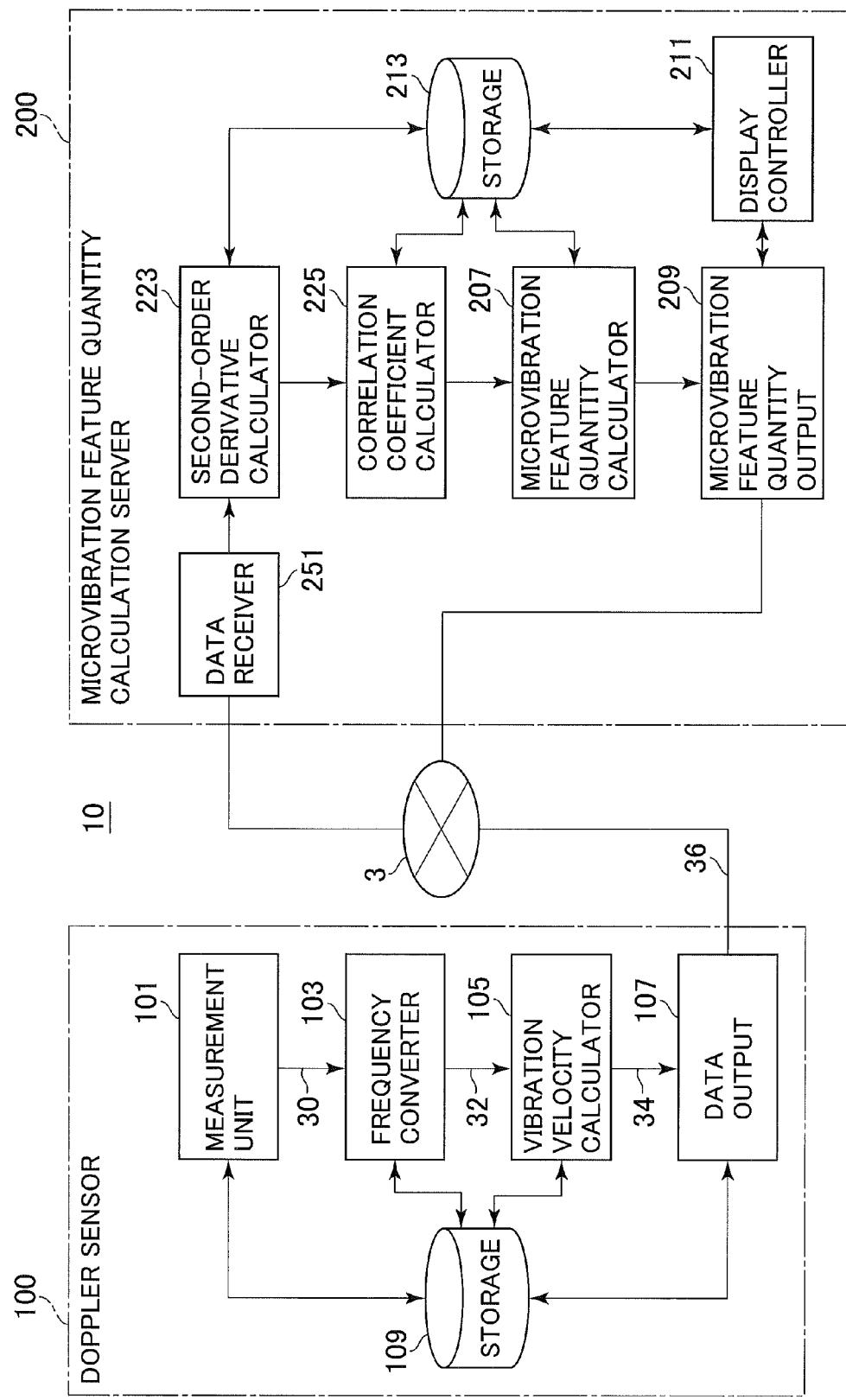
FIG. 9 is also a schematic block diagram showing a further alternative embodiment of the microvibration feature quantity apparatus together with an exemplified configuration of the Doppler sensor.

FIG. 9 shows another alternative embodiment of the invention where some of the functions of the microvibration feature quantity apparatus are installed in the Doppler sensor 100 as described above and a microvibration feature quantity may be calculated by a microvibration feature quantity calculation server connected over a telecommunications network 3, such as the Internet.

The Doppler sensor 100 in the instant alternative embodiment may generally include a measurement unit 101 adapted for detecting a beat signal, a frequency converter 103 adapted to transform the beat signal 30 produced by the measurement unit 101 into a frequency-domain signal, a vibration velocity calculator 105 adapted to use the frequency-domain signal 32 to which the beat signal is transformed to derive a vibration velocity 34, a data output subsection 107 that outputs data 36 on the vibration velocity calculated by the vibration velocity calculator 105, and a storage 109 serving as a memory.

The frequency converter 103 and the vibration velocity calculator 105 may have the same functions and operations as the frequency converter 203 and the vibration velocity calculator 221, respectively, which are included in the microvibration feature quantity apparatus 200 according to the illustrative embodiment shown in and described with reference to FIG. 2, and repetitive description thereof will be avoided.

The data output subsection 107 is adapted to monitor the vibration velocity of microvibration momentarily output from the vibration velocity calculator 105 to produce, when the amount of change in vibration velocity exceeds a predetermined threshold value, data 36 to the microvibration feature quantity calculation server over the network 3.

According to the instant alternative embodiment, the microvibration feature quantity calculation server 200 includes a data receiver 251, which is adapted to receive or obtain data on a vibration velocity transmitted from the Doppler sensor 100 over the network 3 to output the data to the second-order derivative calculator 223.

The microvibration feature quantity calculation server 200 may include the second-order derivative calculator 223, the correlation coefficient calculator 225, the microvibration feature quantity calculator 207, the microvibration feature quantity output subsection 209, the display controller 211, and the storage 213, which may be the same in configuration and operation as of the respective components of the microvibration feature quantity apparatus 200 according to the illustrative embodiment shown in FIG. 2. Repetitive descriptions thereof will be refrained from.

In the present alternative embodiment, the Doppler sensor 100 and the microvibration feature quantity calculation server 200 are thus connected to each other over the network 3, and the Doppler sensor 100 is designed to produce data on vibration velocity when the condition for the predetermined threshold value is satisfied. That makes possible to reduce data communication traffic, and hence efficiently utilize the limited communication band resources.

Figure 10:
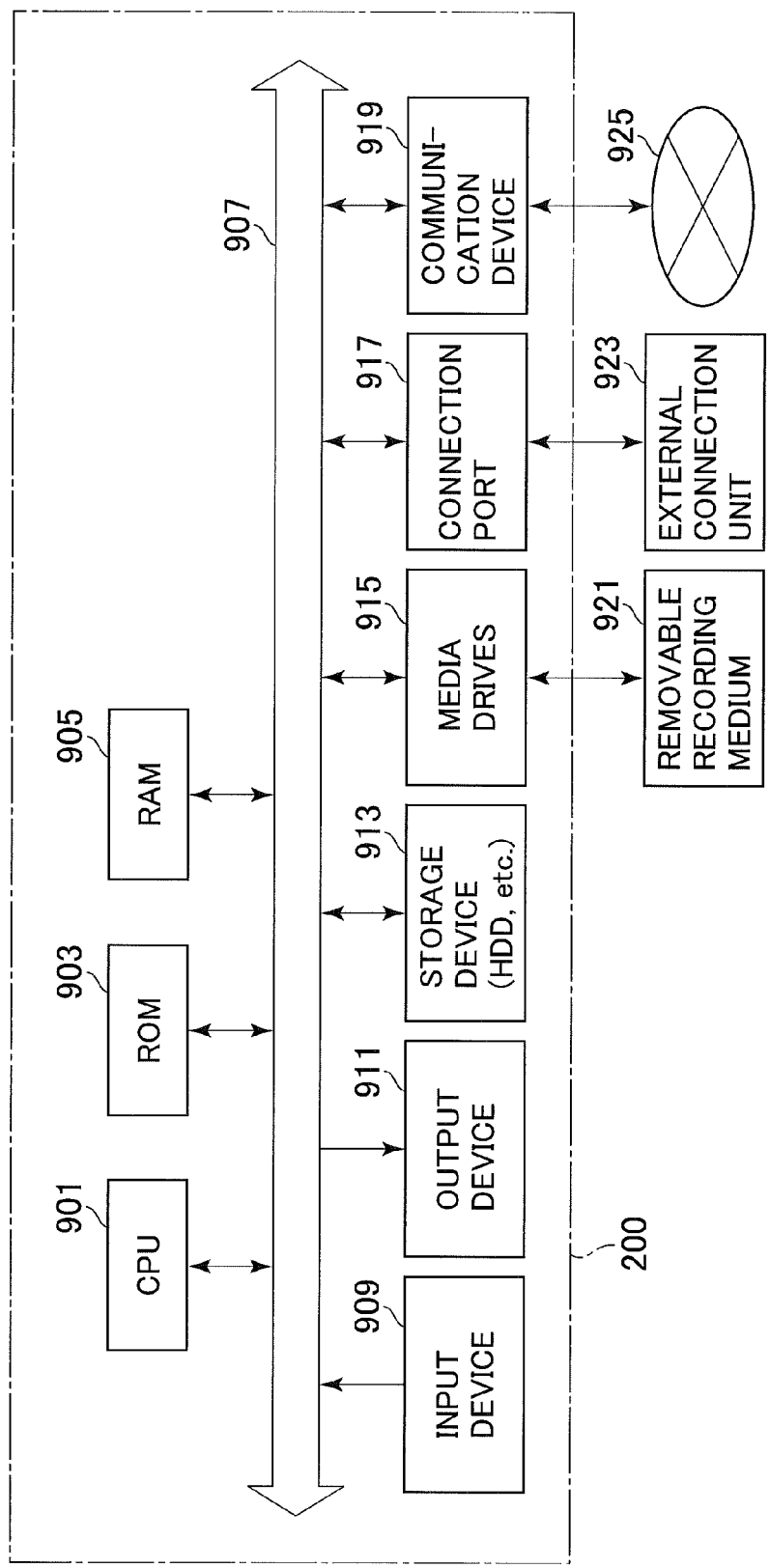
FIG. 10 is a schematic block diagram showing a hardware configuration of the microvibration feature quantity apparatus according to the illustrative embodiment shown in FIG. 1.

The alternative embodiments according to the present invention have thus briefly been described with reference to FIGS. 8 and 9. Now, with reference to FIG. 10, an example of hardware configuration of the microvibration feature quantity apparatus 200 according to the embodiments will be described in detail. FIG. 10 is a schematic block diagram of the hardware configuration of the microvibration feature quantity apparatus 200 according to the embodiments.

The microvibration feature quantity apparatus 200 may generally be implemented by a CPU 901, a ROM 903, and a RAM 905. The microvibration feature quantity apparatus 200 may further include a bus 907, an input device 909, an output device 911, a storage device 913, media drives 915, a connection port 917, and a communication device 919.

The CPU 901 functions as arithmetic processing and control, and is operative under the control of various program sequences stored in the ROM 903, the RAM 905, the storage device 913 or a removable recording medium 921 to control the operation of the entire microvibration feature quantity apparatus 200 or some of the components of the apparatus 200. The ROM 903 is adapted for storing program sequences, arithmetic parameters and the like for use in the CPU 901. The RAM 905 temporarily stores program sequences for use in the CPU 901, as well as parameters and the like appropriately changeable when executing the program sequences. Those components are interconnected by the bus 907, which may be an internal bus, such as a CPU bus.

The bus 907 may be interconnected to an external bus, such as a PCI (Peripheral Component Interconnect/Interface) bus, by a bridge, not shown.

The input device 909 may be manually operable means, such as a mouse, a keyboard, a touch panel, buttons, switches, or levers. Additionally or alternatively, the input device 909 may be, for example, remote control means, so-called remote controller handset, utilizing infrared rays or other electromagnetic waves, or may be an external connection unit 923, such as a PDA (Personal Digital Assistant), adapted for operating the microvibration feature quantity apparatus 200, or a tablet, computer. Moreover, the input device 909 may include, for example, an input control circuit or the like that is responsive to information input by the user on the above-described operating means to produce a corresponding input signal to the CPU 901. The user of the microvibration feature quantity apparatus 200 may operate the input device 909 so as to input various data and instructions on processing operations to the microvibration feature quantity apparatus 200.

The output device 911 may be a human-machine interface device which is capable of visually or aurally notifying the user of the obtained information. As such a device, there may be available visual display devices, such as a CRT (Cathode Ray Tube) display device, a liquid crystal display device, a plasma display device, an EL (Electro-Luminescence) display device and a lamp, and hard copy devices, such as a printer, a mobile telephone and a facsimile device, as well as acoustic devices, such as a loudspeaker and a earphone, and the like. The output device 911 may be adapted for outputting, for example, results from various processing executed by the microvibration feature quantity apparatus 200. Specifically, the display device may display results from various processing executed by the microvibration feature quantity apparatus 200 in the form of texts or images. The acoustic output device converts audio signals representative of reproduced voice data, acoustic data and the like to corresponding analog signals to output the latter in audible sound.

The storage device 913 is adapted for storing data. As examples of storage for use in the microvibration feature quantity apparatus 200, there may be available, for example, a magnetic storage device, such as an HDD (Hard Disk Drive), a semiconductor storage device, an optical storage device, a magneto-optical storage device, or the like. The storage device 913 may store program sequences to be executed by the CPU 901, various kinds of data to be used by the CPU 901, and various kinds of data received from the outside.

The media drives 915 may include a reader/writer for recording media, and built in or externally mounted on the microvibration feature quantity apparatus 200. The drives 915 are adapted to read out information recorded on a mounted magnetic disk, optical disk, or magneto-optical disk, or on the removable recording medium 921, such as a semiconductor memory, to output the information to the RAM 905. Further, the drives 915 are capable of writing records on a mounted magnetic disk, optical disk, or magneto-optical disk, or on the removable recording medium 921, such as a semiconductor memory. The removable recording medium 921 may be, for example, a CD (Compact Disk), a DVD (Digital Versatile Disk), a Blu-ray disk or the like. The removable recording medium 921 may also be a compact flash (CF, trademark), a flash memory, an SD (Secure Digital) memory card, or the like. Further, the removable recording medium 921 may be, for instance, an IC (Integrated Circuit) card having a noncontact IC chip on board, electronic appliance, or the like.

The connection port 917 is for use in directly connecting electronic equipment to the microvibration feature quantity apparatus 200. As an example of the connection port 917, there may be available an USB (Universal Serial Bus) port, an IEEE (The Institute of Electrical and Electronics Engineers) 1394 port, an SCSI (Small Computer System Interface) port, an RS-232C (Recommended Standard 232 version C) port, or the like. When the external connection equipment 923 is connected to the connection port 917, the microvibration feature quantity apparatus 200 may receive various data directly from the external connection equipment 923, or send various data to the external connection equipment 923.

The communication device 919 serves as, for example, a communication interface including a communication unit or the like for establishing a communication connection or link to a communication network 925. The communication device 919 may be, for example, a communication circuit card for use in wired or wireless LAN (Local Area Network), Bluetooth (registered trademark), WUSB (Wireless USB), or the like. The communication device 919 may include a router for optical communication, a router for ADSL (Asymmetric Digital Subscriber Line), various kinds of modem for communications, or the like. The communication device 919 may be adapted for transmitting and receiving signals according to a predetermined protocol, such as TCP/IP (Transmission Control Protocol/Internet Protocol), to and from, e.g. the Internet or other telecommunications equipment. The telecommunications network 925 connectable to the communication device 919 may be in the form of wired or wireless network or the like, which may be the Internet, a home LAN, an infrared communication network, a radio wave communication network, a satellite communication network, or the like.

Thus, the example of hardware configuration capable of implementing the functions of the microvibration feature quantity apparatus according to the illustrative embodiments has been described. The respective components described above may be of general-purpose devices, or alternatively or additionally be of hardware specifically designed for those functions. It is thus possible to appropriately modify the hardware configuration available in accordance with the state of art existing when implementing those embodiments.

In summary, the microvibration feature quantity apparatus according to the illustrative embodiments of the present invention utilizes the reversible linear relationship established between the output frequency of a Doppler sensor and the velocity of an object to be measured due to the Doppler effect to deal with microvibration as a change in Doppler frequency, and hence in vibration velocity, to derive the second-order derivative with respect to time of the vibration velocity of microvibration to identify an abrupt change. That makes it possible to accurately calculate a feature quantity relating to microvibration raised in an object to be measured, regardless of the environment of measuring microvibration.

Specifically, in a case where human heartbeat is dealt with as microvibration, the microvibration detecting apparatus according to the illustrative embodiments may be set on a desk in an office or the like, thereby making it possible to observe fluctuation in heartbeat while working on the desk in a noncontact manner. Further, the microvibration detecting apparatus according to the embodiments may be arranged in the reception hall of a hospital or the like to observe patients waiting for examination in terms of heartbeat fluctuation so as to identify patients to be examined more urgently than the rest, which may be useful especially for triage in a large-scale disaster.

The Doppler sensor of the embodiments may be mounted on a chair, a bed or the like so as to carry out measurement in a contact state. It is thus possible to more accurately measure heartbeat while a person sits on the chair or lies down on the bed.

Further, the microvibration feature quantity detecting apparatus and the microvibration feature quantity apparatus according to the illustrative embodiments are capable of analyzing not only microvibration raised by the vital activities of human being but also instantaneous vibrations or oscillation caused in a variety of living and material bodies in a noncontact manner.

The entire disclosure of Japanese patent application No. 2011-77999 filed on Mar. 31, 2011, including the specification, claims, accompanying drawings and abstract of the disclosure, is incorporated herein by reference in its entirety.

While the present invention has been described with reference to the particular illustrative embodiments, it is not to be restricted by the embodiments. It is to be appreciated that those skilled in the art can change or modify the embodiments without departing from the scope and spirit of the present invention.

What I claim is:

1. An apparatus for calculating microvibration feature quantity, comprising:
   a beat signal receiver that receives a beat signal output from a Doppler sensor, the Doppler sensor radiating a radiation wave at a predetermined frequency to a body and sensing part of the radiation wave reflected by the body to output the beat signal at a frequency associated with a difference in frequency between the radiation wave and the reflected part;
   a frequency converter that transforms the received beat signal to a corresponding frequency-domain signal; and
   a beat signal feature quantity calculator which uses the frequency-domain signal to derive a beat signal feature quantity exhibiting an abrupt change with respect to time of a vibration velocity of the microvibration,
   said beat signal feature quantity calculator deriving the beat signal feature quantity by calculating a second-order derivative with respect to time of the vibration velocity and emphasizing the microvibration from a temporal change of the vibration velocity.

2. The apparatus in accordance with claim 1, further comprising a microvibration feature quantity calculator which uses the derived beat signal feature quantity to obtain a microvibration feature quantity including at least one of a temporal position of the microvibration, an interval of the microvibration and a frequency of vibration of the microvibration.

3. The apparatus in accordance with claim 1, wherein said beat signal feature quantity calculator obtains a beat signal in a predetermined frequency range from the frequency-domain signal to derive the beat signal feature quantity.

4. The apparatus in accordance with claim 1, wherein the frequency-domain signal includes a frequency component in the beat signal, the frequency component being dealt with a frequency change caused by a Doppler effect to be converted into a velocity, with which a weighted averaging is conducted on a power of the frequency component to thereby calculate the vibration velocity in a predetermined frequency range.

5. The apparatus in accordance with claim 1, wherein the frequency-domain signal includes a frequency component in the beat signal, the frequency component being averaged with a weight corresponding to a power of the frequency component to thereby calculate the vibration velocity in a predetermined frequency range.

6. A method for calculating a microvibration feature quantity comprising:
   obtaining a beat signal output from a Doppler sensor, the Doppler sensor radiating a radiation wave at a predetermined frequency to a body and sensing part of the radiation wave reflected by the body to output the beat signal at a frequency associated with a difference in frequency between the radiation wave and the reflected part;
   transforming the received beat signal to a corresponding frequency-domain signal;
   using the frequency-domain signal to derive a beat signal feature quantity exhibiting an abrupt change with respect to time of a vibration velocity of the microvibration; and
   deriving the beat signal feature quantity by calculating a second-order derivative with respect to time of the vibration velocity and emphasizing the microvibration from a temporal change of the vibration velocity.

7. A non-transitory computer readable recording medium having a computer program stored for controlling a computer, when run on the computer, to function as an apparatus for calculating microvibration feature quantity by:
   obtaining a beat signal output from a Doppler sensor, the Doppler sensor radiating a radiation wave at a predetermined frequency to a body and sensing part of the radiation wave reflected by the body to output the beat signal at a frequency associated with a difference in frequency between the radiation wave and the reflected part;
   transforming the received beat signal to a corresponding frequency-domain signal;
   using the frequency-domain signal to derive a beat signal feature quantity exhibiting an abrupt change with respect to time of a vibration velocity of the microvibration; and
   deriving the beat signal feature quantity by calculating a second-order derivative with respect to time of the vibration velocity and emphasizing the microvibration from a temporal change of the vibration velocity.

* * * * *